United States Patent
Crudo

(10) Patent No.: US 6,659,770 B2
(45) Date of Patent: Dec. 9, 2003

(54) IMPLANT FOR FIXING DENTAL PROSTHESES

(76) Inventor: Vincenzo Crudo, Via Tiepolo, 36, 36071 Arzignano (IT)

( * ) Notice: Subject to any disclaimer, the term of this patent is extended or adjusted under 35 U.S.C. 154(b) by 68 days.

(21) Appl. No.: 09/949,618

(22) Filed: Sep. 12, 2001

(65) Prior Publication Data

US 2002/0031748 A1 Mar. 14, 2002

(30) Foreign Application Priority Data

Sep. 12, 2000 (IT) .................................. PD2000A0218

(51) Int. Cl.7 .............................................. A61C 8/00
(52) U.S. Cl. ................................................... 433/173
(58) Field of Search ............................ 433/172, 173, 433/174, 175, 176

(56) References Cited

U.S. PATENT DOCUMENTS

| | | | |
|---|---|---|---|
| 4,542,539 A | * 9/1985 | Rowe, Jr. et al. | 623/16 |
| 5,246,370 A | 9/1993 | Coatoam | 433/173 |
| 5,281,140 A | * 1/1994 | Niznick | 433/172 |
| 5,782,918 A | * 7/1998 | Klardie et al. | 433/173 |
| 5,947,733 A | 9/1999 | Sutter et al. | 433/173 |
| 6,102,703 A | 8/2000 | Day | 433/174 |

FOREIGN PATENT DOCUMENTS

| | | |
|---|---|---|
| DE | 197 53 577 | 6/1999 |
| WO | 01 28451 | 4/2001 |

* cited by examiner

Primary Examiner—John J. Wilson
(74) Attorney, Agent, or Firm—Guido Modiano; Albert Josif; Daniel O'Byrne

(57) ABSTRACT

An improved implant for fixing dental prostheses, of the type constituted by an intrabony section that is fixed, upon assembly, within the gum, and to which a dental prosthesis anchoring superstructure is fixed; the superstructure is constituted by an abutment provided with an axial through hole that is partially accommodated in a seat formed in the intrabony section and suitable to provide the support around which the tooth is constituted, and an abutment fixing pin that is inserted axially in the abutment and is provided with a threaded portion that is associated, upon assembly, with a threaded blind hole formed axially in the bottom of the seat. The seat has a portion provided with a triangular cross-section with radiused vertices and coupled, upon assembly, to a complementarily shaped portion of a shank formed in the abutment element. The seat and the shank are complementarily shaped and provided with a circular cross-section in their remaining parts as well.

4 Claims, 2 Drawing Sheets

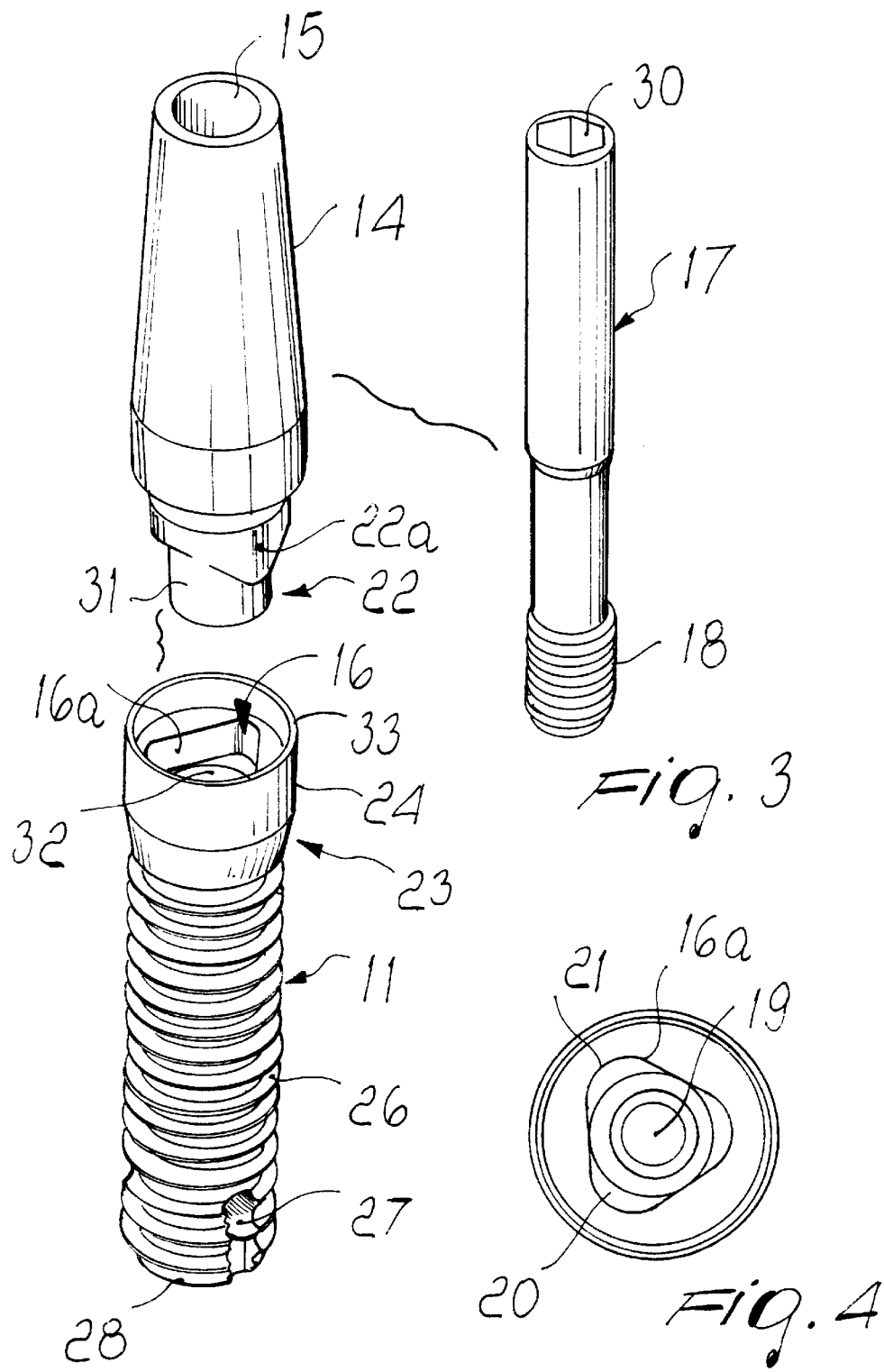

IMPLANT FOR FIXING DENTAL PROSTHESES

BACKGROUND OF THE INVENTION

The present invention relates to an improved implant for fixing dental prostheses.

It is known that implants for fixing dental prostheses substantially constituted by an intrabony section that is fixed upon assembly inside the bony part of the gum are currently particularly appreciated owing to their biotechnological characteristics.

A superstructure for anchoring the prosthesis is fixed to the intrabony section and is constituted by an abutment provided with an axial through hole accommodated in a seat formed in the intrabony section and suitable to provide the support around which the tooth is formed.

The superstructure normally also comprises an abutment fixing pin that is inserted axially in said abutment and is provided with a threaded portion that is associated, upon assembly, with a threaded blind hole formed axially in the bottom of said seat.

Currently, the coupling of said seat, which usually has a polygonal profile, particularly a hexagonal one, occurs by means of a complementarily shaped shank formed in said abutment.

However, these polygonal couplings between the intrabony section and the superstructure do not ensure perfect stability of the tooth, particularly in relation to rotation-preventing and extrusion-preventing functions.

It is in fact known that a tooth, during mastication, is subjected to intense mechanical stresses that require stable lockings and the total absence of mutual rotations between the dental prosthesis and the gum, on penalty of a drastic reduction of the functionality of said dental prosthesis, with considerable associated discomfort for the individual.

For this purpose, an implant has been devised which is disclosed in Italian patent No. 1288004 of Dec. 5, 1996 and is constituted by an intrabony section that is fixed, upon assembly, within the gum and to which a superstructure for anchoring the prosthesis is fixed.

Said structure is constituted by an abutment, which is provided with an axial through hole, is partially accommodated in a seat formed in said intrabony section, and is suitable to provide the support around which the tooth is constituted, and by an abutment fixing pin, which is inserted axially therein and has a threaded portion associated upon assembly with a threaded blind hole formed axially in the bottom of said seat.

Said seat has a portion that has a substantially triangular cross-section with radiused vertices and is coupled, upon assembly, to a complementarily shaped portion of a shank formed in the abutment element so as to provide, as a whole, a rotation-preventing and extrusion-preventing connection between the intrabony section and the superstructure.

The seat and the shank are also complementarily shaped and provided with a hexagonal cross-section in their remaining parts.

Although the cited implant constitutes an undisputed improvement with respect to the known art, since it provides total safety in the coupling between the intrabony section and the superstructure without the risk of mutual axial rotations thereof, said implant has shown in practice a considerable drawback that has prevented its diffusion.

Because of the hexagon-to-hexagon coupling combined with the triangle-to-triangle coupling, whose radiused vertices correspond to three alternated sides of the corresponding hexagons, during installation of the abutment, which is mostly performed without direct viewing, there is a 50% chance of choosing the incorrect mutual coupling position.

Accordingly, there is a 50% chance of fixing the implant badly, with consequent inconvenience and problems for the patient.

SUMMARY OF THE INVENTION

The aim of the present invention is to provide an implant for fixing dental prostheses to the gum that totally solves the problem noted above in the implant related to patent 1288004.

Another object of the present invention is to provide an implant whose structure is particularly easy to apply to the bony part of the gum and has, in its active configuration, high functionality and compatibility with the requirements of the individual.

Another object of the present invention is to provide an implant having a high degree of biocompatibility and suitable to simplify fitting on the part of the operator.

Another object of the present invention is to provide an implant whose costs are furthermore competitive with those of known implants.

Another object of the present invention is to provide an implant that can be manufactured with known technologies.

This aim and these and other objects that will become better apparent hereinafter are achieved by an improved implant for fixing dental prostheses, of the type constituted by an intrabony section that is fixed, upon assembly, within the bony part of the gum, and to which a tooth anchoring superstructure is fixed, said superstructure being constituted by an abutment provided with an axial through hole that is partially accommodated in a seat formed in said intrabony section and suitable to provide the support around which the prosthesis is constituted, and an abutment fixing pin that is inserted axially in said abutment and is provided with a threaded portion that is associated, upon assembly, with a complementarily threaded blind hole formed axially in the bottom of said seat, said seat having a portion provided with a triangular cross-section with radiused vertices and coupled, upon assembly, to a complementarily shaped portion of a shank formed in the abutment element, said implant being characterized in that said seat and said shank are complementarily shaped and provided with a circular cross-section in their remaining parts as well.

BRIEF DESCRIPTION OF THE DRAWINGS

Further characteristics and advantages of the present invention will become better apparent from the description of two embodiments thereof, illustrated only by way of non-limitative example in the accompanying drawings, wherein:

FIG. 3 is an exploded view of the implant of FIG. 1;

FIG. 4 is another orthographic projection view of the implant of FIG. 1.

DESCRIPTION OF THE PREFERRED EMBODIMENTS

Figures 1, 2:
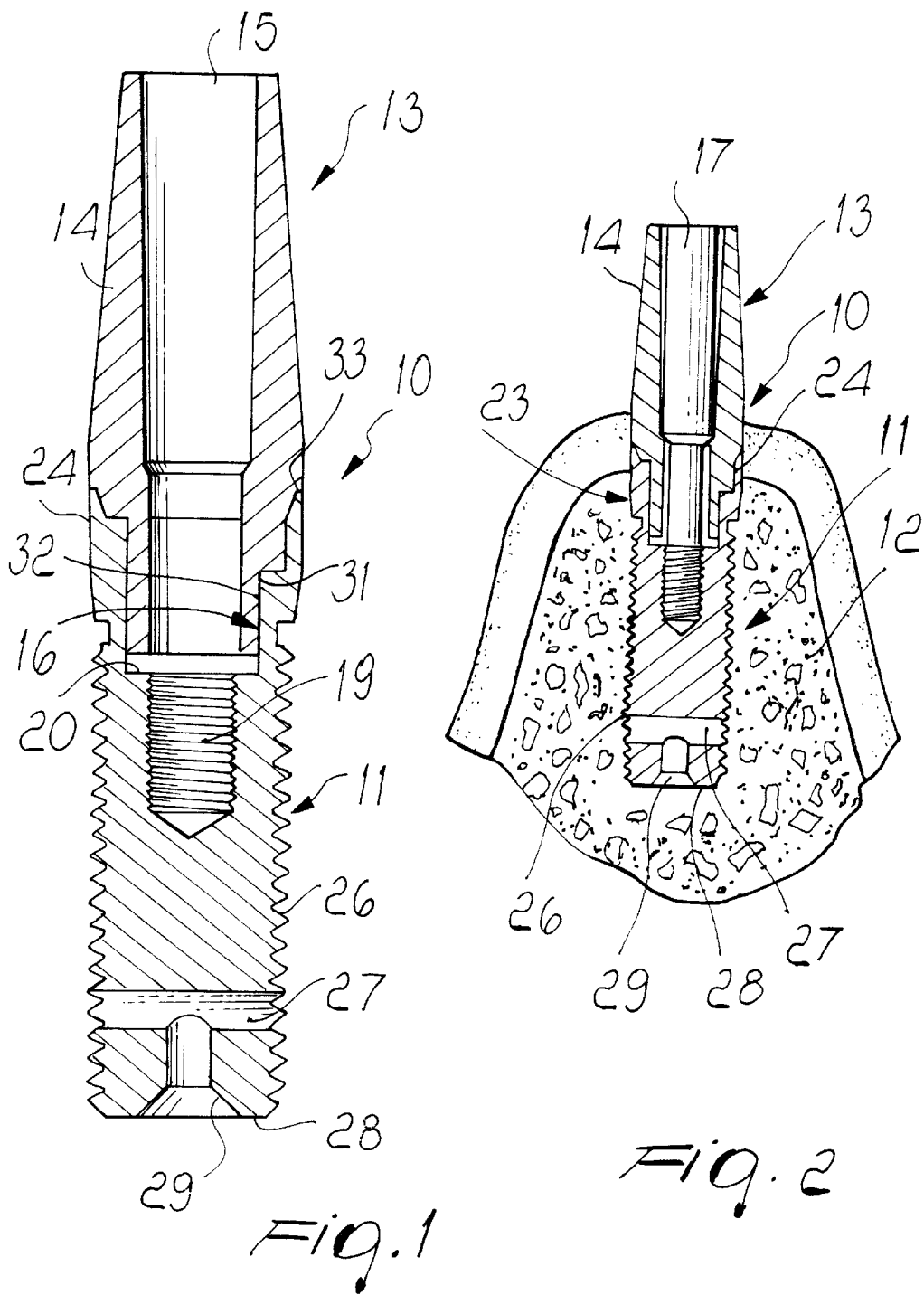
FIG. 1 is a sectional orthographic projection view of a first embodiment of an implant according to the invention.
FIG. 2 is a view of the implant of FIG. 1 applied to the gum.

With particular reference to FIGS. 1 to 4, an improved implant for fixing dental prostheses is generally designated by the reference numeral 10.

The implant 10 is constituted by an intrabony section, generally designated by the reference numeral 11 and described in greater detail hereinafter, which is fixed upon assembly within the bony part of the gum 12; a superstructure, generally designated by the reference numeral 13, for anchoring the prosthesis, which is not shown, is fixed to said section and is constituted by an abutment 14 provided with an axial through hole 15 that is accommodated in a seat 16 formed in the intrabony section 11 and is suitable to provide the support around which the tooth is formed.

The superstructure 13 also comprises an abutment fixing pin 17, which is inserted axially in said abutment and is provided with a threaded portion 18 that is associated, upon assembly, with a complementarily threaded blind hole 19 formed in the bottom 20 of the seat 16.

The seat 16 has a portion 16a that has a substantially triangular cross-section, as shown particularly clearly in FIG. 4, with radiused vertices 21, and is coupled upon assembly, axially and without play, to a complementarily shaped portion 22a of a shank 22 formed in the abutment 14, so as to provide a rotation-preventing and extrusion-preventing connection between said intrabony section 11 and said superstructure 13.

According to the invention, the remaining parts 31 and 32 of the seat 16 and of the shank 22 are also complementarily shaped and provided with a circular cross-section or likewise have a conical shape.

The intrabony section 11, in this case, is substantially constituted by a cylindrical element 23, which is shaped so as to form, at the end that upon assembly is directed toward the outside of the gum, a transgingival collar 24 that is flared and at which the seat 16 is formed axially.

The collar 24 has a rim that is shaped so as to form a flat ring 33 for supporting a complementarily shaped portion of said abutment 14.

Furthermore, the cylindrical element 23, in this case, is shaped externally, except for the collar 24, so as to form a thread 26 that is suitable to provide an implant that is self-tapping in the bony part of the gum 12.

The cylindrical element 23 is provided with holes 27 for discharging the apical pressure and with an internal apex 28 provided with a frustum-shaped cavity 29.

Moreover, the cylindrical element 23 can be covered by a titanium plasma flash.

The pin 17 is provided with an axial blind hole 30 that is open outward and has a hexagonal cross-section for the mating of a hexagonal key for screwmg-in.

In practice it has been observed that the present invention has achieved the intended aim and objects; in particular, it should be noted that the complementary shaping of the parts 31 and 32 having a circular cross-section eliminates the danger of coupling errors during the fitting of the implant.

Further, the overall structural simplicity of the implant is matched by a coupling between the intrabony section and the superstructure that entails no risk of mutual axial rotations.

It should also be noted that the structure of the implant according to the invention ensures the extrusion-resistance of the assembly.

Attention is also called to the great biocompatibility of the assembly constituted by the implant according to the invention, which ensures perfect functionality and toughness.

The present invention is susceptible of numerous modifications and variations, all of which are within the scope of the inventive concept.

All the details may furthermore be replaced with other technically equivalent elements.

The materials, so long as they are compatible with the contingent use, as well as the dimensions, may be any according to requirements.

The disclosures in Italian Patent Application No. PD2000A000218, from which this application claims priority, are incorporated herein by reference.

What is claimed is:

1. An improved implant for fixing dental prostheses, of the type constituted by an intrabony section that is fixed, upon assembly, within the bony part of the gum, and to which a tooth anchoring superstructure is fixed, said superstructure being constituted by an abutment provided with an axial through hole that is partially accommodated in a seat formed in said intrabony section and suitable to provide the support around which the prosthesis is constituted, and an abutment fixing pin that is inserted axially in said abutment and is provided with a threaded portion that is associated, upon assembly, with a complementarily threaded blind hole formed axially in the bottom of said seat, said seat having a portion provided with a triangular cross-section with radiused vertices and coupled, upon assembly, to a complementarily shaped portion of a shank formed in the abutment element, said seat and said shank being complementarily shaped and being provided with remaining parts which are located respectively below said portion with triangular cross-section of said seat and below said complementarily shaped portion of said shank and which are mutually complementarily shaped and provided with a circular cross-section, said intrabony section having, at the end that upon assembly is directed toward the outside of the gum, a flared transgingival collar at which said seat is formed axially, said collar having a rim that is shaped so as to form a flat resting ring for a complementarily shaped portion of said abutment, said transgingival collar and said collar forming a continuous cylindrical outer surface upon assembly in the region adjacent said flat resting ring and said complementarily shaped portion of said abutment, said transgingival collar having an internally conical portion extending below said flat resting ring and a further flat resting portion arranged below said internally conical portion upon which a complimentarily shaped flat portion of said abutment rests upon assembly.

2. The implant according to claim 1, wherein said seat and said shank are conical.

3. The implant according to claim 1, wherein the outer surface of said cylindrical element is contoured, except for said collar, so as to form a thread suitable to provide an implant that is self-tapping in the gum.

4. The implant according to claim 1, wherein said cylindrical element is coated by a titanium plasma spray flash.

* * * * *